United States Patent [19]

Okazaki et al.

[11] 4,066,787

[45] Jan. 3, 1978

[54] STABILIZED PROSTAGLANDIN COMPOSITION AND THE PROCESS FOR THE PREPARATION THEREOF

[75] Inventors: Kiyoshi Okazaki; Hiroitsu Kawada, both of Kawagoe; Hidemi Shimizu, Ageo; Tadayoshi Ohmura, Niiza; Jun Sekino, Kashiwa, all of Japan

[73] Assignee: Yamanouchi Pharmaceutical Co., Ltd., Tokyo, Japan

[21] Appl. No.: 798,017

[22] Filed: May 18, 1977

[30] Foreign Application Priority Data

May 21, 1976 Japan .................................. 51-58702

[51] Int. Cl.² .................... A61K 31/19; A61K 31/215

[52] U.S. Cl. ..................................... 424/317; 424/305
[58] Field of Search ................................ 424/305, 317

[56] References Cited

U.S. PATENT DOCUMENTS 3,954,787    5/1976    Monkhouse ......................... 424/317

Primary Examiner—Sam Rosen
Attorney, Agent, or Firm—Burgess, Ryan and Wayne

[57] ABSTRACT

A dried and stabilized prostaglandin composition containing a prostaglandin E group compound with calcium lactate and/or amylopectin, and a stabilized pharmaceutical preparation for practical administration prepared from the said composition.

9 Claims, No Drawings

STABILIZED PROSTAGLANDIN COMPOSITION AND THE PROCESS FOR THE PREPARATION THEREOF

BACKGROUND OF THE INVENTION

1. Field of the Invention

The present invention relates to a dried and stabilized composition of a prostaglandin E group compound (hereinafter, it is referred to as PGE group compound) and to the process for the preparation thereof. More particularly, the invention relates to a dried and stabilized PGE group composition prepared from a PGE group compound with calcium lactate and/or amylopectin.

The composition of the present invention is particularly advantageous for pharmaceutical preparations.

Further, the invention relates to a stabilized pharmaceutical preparation prepared from the abovementioned dried and stabilized PGE group composition and to the process for the preparation thereof.

PGE group compounds are shown by the following basic structural formula

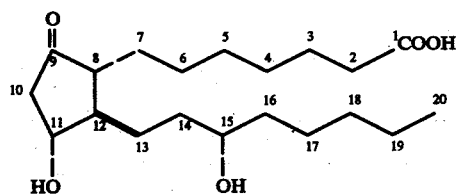

The compounds having the above described basic structure are characterized by the oxo group at position 9 and the hydroxy group at position 11, and include $PGE_1$, $PGE_2$, $PGE_3$, etc. which are named according to the number and position of the double bond in the molecule. PGE group compounds in this invention include the compounds having substituent(s) such as the methyl group, methoxy group, hydroxy group, oxo group, etc. at various position(s) of the structure. Suitable examples are 16-methyl-$PGE_2$, 3-methyl-$PGE_2$, 3,6(R)-dimethyl-$PGE_2$, 17-oxo-15-epi-$PGE_2$, 16(R)-hydroxy-$PGE_2$, 15(R)-methyl-$PGE_2$ methyl ester, 15(S)-methyl-$PGE_2$ methyl ester, 16,16-dimethyl-$PGE_2$ methyl ester, 4(R),16(R)-dimethyl-$PGE_2$, 4(R),16(S)-dimethyl-$PGE_2$, 4(S),16(R)-dimethyl-$PGE_2$, 4(S),16(S)-dimethyl-$PGE_2$, 16(R,S)-methyl-20-methoxy-$PGE_2$, 16(S)-methyl-20-methoxy-$PGE_2$.

2. Description of the Prior Art

The PGE group compounds exhibit, even at a small dose, various physiological effects such as control of the contractive force of uterus, hypotensive activity, treatment and prophylaxis of digestive organ ulcers, control of lipid metabolism, bronchodilator activity, etc.

However, the application of PGE group compounds in a number of areas has been severely hampered by their instability, especially in solution. (see Brummer; J. Pharm. Pharmacol., 23, 804–805 (1971) and Karmin et al; European J. Pharmacol., 4, 416–420 (1968))

For the preparation of a stable composition of $PGE_2$, several methods are heretofore known; U.S. Pat. No. 3,749,800 describes a concentrated stock solution of $PGE_2$ in an anhydrous, water miscible, pharmacologically-acceptable alcohol; Belgian Pat. No. 790,840 describes a solution in an anhydrous organic aprotic dipolar solvent such as N,N-dimethylacetamide. These methods are applied for the concentrated preparation of injections and this preparation is diluted on the occasion of administration. In U.S. Pat. No. 3,851,052, there is disclosed a stabilized PGE group composition with an alkali metal sulfite salt, however, the stabilization effect by the method is limited to a stock solution of a PGE group compound in alcohol together with an alkali metal sulfite salt and the potency of the solution becomes only about 70% when the solution is stored for 13 days at 60° C.

U.S. Pat. No. 3,826,823 discloses a solid dispersion of prostaglandin in polyvinyl pyrrolidone (PVP). In this process highly hygroscopic PVP is apt to absorb moisture in the air and consequently, the solid dispersion is difficult to pulverize and tends to be sticky by the absorption of moisture in the air. Moreover, PVP is reported to cause hepatotoxicity and can not be suitable for pharmaceutical preparations.

U.S. Pat. No. 3,903,297 discloses substituted prostaglandin derivatives and their formulations; however the stability of the formulations are not mentioned.

U.S. Pat. No. 3,917,864 refers to the lyophilized composition of prostaglandin $F_{1\alpha}$ together with mannitol.

In German Offenlegungsschrift No. 2,451,161, some of the present inventors had invented a stabilized prostaglandin composition with the addition of thiol compounds, dextrin, dextran, lower alkyl cellulose or salt of deoxycholic acid.

OBJECTS OF THE INVENTION

The primary object of the present invention is to provide dried and stabilized prostaglandin compositions. It is a further object of the present invention to provide novel compositions containing a PGE group compound with calcium lactate and/or amylopectin. It is a further object of this invention to provide the compositions which can be prepared in simple and easily operable preparation process suitable for industrial production. It is a further object of this invention to provide the pharmaceutical preparations containing the above prostaglandin compositions for practical administration.

DETAILED DESCRIPTION OF THE INVENTION

The composition of this invention comprises a PGE group compound with calcium lactate and/or amylopectin, and the preferred content of calcium lactate or amylopectin is 2–2000 parts by weight per 1 part by weight of a PGE group compound. The composition of this invention is generally prepared in the following manner; that is, a PGE group compound is dissolved in water, or an organic solvent such as methanol, ethanol, dioxane, or a mixture thereof, together with calcium lactate and/or amylopectin, the pH of the solution is adjusted to 2–8.5 when water is used as the solvent, and after treatment with an ordinary method such as filtration, etc., the product is dried by a conventional method such as lyophilization, drying under ventilation, vacuum drying, spray drying, etc., to form a dry powder.

In addition, since the PGE group compound requires a long period of time for complete dissolution in water, though it is soluble in water, it is preferred, in the case of dissolving a PGE group compound in water, to apply a pre-treatment for increasing the contact area of a PGE group compound with water in the dissolution vessel by once dissolving a PGE group compound in an organic solvent such as ethanol, ethyl acetate, etc., and then distilling off the solvent to form a thin film spread over the inside surface of the vessel.

The invention also relates to various kinds of pharmaceutical preparations prepared using the above-described PGE group compositions, for example, tablets, granules, powders, capsules, injections, troches, pills, suppositories, ointments, packs, liniments, dry syrups. These preparations are prepared by adding, if necessary, ingredients or additives such as an isotonic agent, a preservative, an analgesic, a binding agent, a disintegrator, a lubricant, an excipient, etc., as well as a coloring agent, a flavor, a tasting agent, etc., to the aforesaid PGE group composition and making preparations using the mixture by a conventional manner.

Calcium lactate used in this invention includes anhydrous and hydrated, for example, penta hydrate and amylopectin means amylocpectin starch, a non linear polymer of glucose known as Amioca (Merck Index 9th Ed. 500 (1976)) and they are added to the PGE group compound either singly or in combination.

The stability and the process for producing the PGE group compositions and pharmaceutical preparations of this invention will be further explained by the following experiment and examples.

STABILITY TEST

Each of the dry compositions in a container shown in Table 1 was dissolved in 1 ml. of water, and after adjusting the pH of the solution to 3 or lower than 3 by adding citric acid, the composition was extracted with ethyl acetate, dried, and then concentrated. Then, the whole amount of the concentrate was subjected to silica gel thin layer chromatography and developed with a mixture of chloroform, methanol, acetic acid, and water (90: 8: 1: 0.8 by volume ratio). Then, an ethanolic solution of 5% molybdic acid was sprayed thereto, after heating for 10 minutes to 105°–110° C. to develop color, the absorbance of spots of a PGE group compound and the decomposition products (the corresponding prostaglandin A group and prostaglandin B group) were measured using a Shimazu Double wave Lengths Chromatoscanner CS-900 (made by K. K. Shimazu Seisakusho), and the content of the prostaglandin E group in the sample was calculated from the peak area ratio of each spot. The remained ratio employed in this calculation is the ratio of the content of a PGE group compound in the sample present in a container after standing for 6 days at 60° C. to the content of a prostaglandin E group compound in the dry composition present in the container prepared in each of Examples 1–8. The results are shown in Table 1.

Table 1

| Prostaglandin E group (25 µg per container) | Stabilizing Agent | agent Amount of one container | Stability test remaining (%) (preserving at 60° C) | | | Ex. No. |
|---|---|---|---|---|---|---|
| | | | 6 days | 14 days | 20 days | |
| 16(S)-methyl-20-methoxy PGE$_2$ (I) | calcium lactate pentahydrate | 30 mg | 82.2 | 70.6 | 64.4 | 1 |
| " | " | 50 mg | 82.0 | 71.6 | 66.5 | 2 |
| " | " | 10 mg | 78.5 | 62.3 | 53.2 | 3 |
| " | none | — | 7.7 | 0 | 0 | — |
| 4(R),16(R)-dimethyl-PGE$_2$ (II) | calcium lactate pentahydrate | 30 mg | 84.8 | | | 4 |
| " | none | — | 6 | | | — |
| 4(S),16(R)-dimethyl-PGE$_2$ (III) | calcium lactate pentahydrate | 30 mg | 85.8 | | | 5 |
| " | none | — | 5.9 | | | — |
| 4(S),16(S)-dimethyl-PGE$_2$ (IV) | calcium lactate pentahydrate | 30 mg | 91.2 | | | 6 |
| " | none | — | 6 | | | — |
| 4(R),16(S)-dimethyl-PGE$_2$ (V) | calcium lactate pentahydrate | 30 mg | 85.8 | | | 7 |
| " | none | — | 6.4 | | | — |
| (I) | amylopectin | 20 mg | 76.0 | | | 8 |
| " | none | — | 7.7 | | | — |

The required amount of additive(s), calcium lactate and/or amylopectin, to a PGE group compound is considerably less than those of known additives.

Further, the dried product of the invention is easily sieved into fine particles without pre-treatment such as grinding or milling and reduces the pulverization step simple.

Therefore the present invention possesses the economical advantages in industrial applications.

The composition of the present invention dissolves instantaneously in water and this high solubility facilitates quick treatment of patients when prepared in the form of an injectable preparation such as a lyophilized ampoule preparation.

The preparations of this invention, when prepared in tablet, granule or powder formulations, dissolve and disintegrate within 4 minutes and release rapidly the medicine, PGE group compound, while conventional preparations generally requires more than ten minutes.

These high solubility and short disintegration time characteristics contribute significantly to the importance of the present compositions as medical preparations.

Following Examples 1–9 illustrate the production of the PGE group compositions of this invention in powder forms.

EXAMPLE 1

In a 2 liter container was placed a solution of 50 mg. of 16(S)-methyl-20-methoxy-prostaglandin E$_2$ (hereinafter, it is referred to as (I)) dissolved in 1 ml. of ethanol and after spreading the solution over the wall of the container, the container was ventilated with nitrogen stream to vaporize off ethanol. Then, 60 g. of calcium lactate and 1500 ml. of distilled water were added to the residue to dissolve calcium lactate and after adjusting the pH of the system by adding sodium hydroxide, (I) was dissolved therein with stirring. Then, distilled water was added to the solution to make a volume of 2000 mls. The solution was filtered and lyophilized in a tray according to conventional procedures. The solid product obtained was sieved.

EXAMPLES 2–9

By following the procedure as in Example 1 under the conditions shown in Table 2, prostaglandin-containing powders were obtained.

Table 2

| Ex. No. | Prostaglandin E group (50 mg) | Additive | (g) | Solvent | (l) | pH | Filtration method | Container at drying | Solvent temp. at drying (° C) | Drying method |
|---|---|---|---|---|---|---|---|---|---|---|
| 2 | (I) | calcium lactate pentahydrate | 100 | water | 2 | 6.5 | aseptic | vial | −40 | lyophilization |
| 3 | (I) | " | 20 | " | " | 6 | conventional | tray | " | " |
| 4a | (II) | " | 60 | " | " | 7 | " | rotary evaporator | 5 | drying under reduced pressure |
| 5 | (III) | " | " | " | " | 3 | " | tray | −40 | lyophilization |
| 6a | (IV) | " | " | " | " | 6 | " | rotary evaporator | 5 | drying under reduced pressure |
| 7 | (V) | " | " | " | " | 7.5 | " | tray | −40 | lyophilization |
| 8 | (I) | amylopectin | 40 | " | " | 6.5 | " | vial | " | " |
| 9 | (I) | calcium lactate pentahydrate, amylopectin | 20<br>40 | " | " | 6 | " | tray | " | " |

The following Examples 10–23 illustrate the process for the preparation of the pharmaceutical preparations of this invention.

EXAMPLES 10–23

Using the prostaglandin-containing powders (referred to as PG-Powd) prepared in Examples 1–9, pharmaceutical preparations having the compositions shown in Table 3 were prepared.

Table 3

| Ex. No. | Ingredient | mg per tablet | Preparation | Remained ratio after 6 days at 60° C (%) |
|---|---|---|---|---|
| 10 | PG-Powd (obtained in Ex. 1) | 30 | | |
| | Crystalline cellulose | 120 | | |
| | Calcium hydrogenphosphate | 87 | tablet (direct compression) | 97 (8) |
| | Carboxymethyl cellulose calcium | 4 | | |
| | Light silicic anhydride | 1 | | |
| | Talc | 4 | | |
| | Magnesium stearate | 4 | | |
| | (This composition is referred to as Composition 1) | | | |
| | | mg per tablet | | |
| 11 | PG-Powd (obtained in Ex. 3) | 10 | | |
| | Crystalline cellulose | 140 | | |
| | Calcium hydrogenphosphate | 87 | tablet (direct compression) | 91 (7) |
| | Carboxymethyl cellulose sodium | 4 | | |
| | Light silicic anhydride | 1 | | |
| | Talc | 4 | | |
| | Magnesium stearate | 4 | | |
| | (This composition is referred to as Composition 2) | | | |
| | | mg per tablet | | |
| 12 | PG-Powd (obtained in Ex. 1) | 30 | | |
| | Crystalline cellulose | 151 | | |
| | Hydroxypropyl cellulose | 3 | tablet (wet granulation) | 93 (7.5) |
| | Starch | 10 | | |
| | Talc | 4 | | |
| | Magnesium stearate | 2 | | |
| | (This composition is referred to as Composition 3) | | | |

Table 3-continued

| Ex. No. | Ingredient | mg per tablet | Preparation | Remained ratio after 6 days at 60° C (%) |
|---|---|---|---|---|
| 13 | PG-Powd (obtained in Ex. 3) | 10 | | |
| | Crystalline cellulose | 171 | | 89 |
| | Hydroxypropyl cellulose | 3 | tablet | (7) |
| | Carboxymethyl cellulose calcium | 10 | (wet granulation) | |
| | Talc | 4 | | |
| | Magnesium stearate | 2 | | |

(This composition is referred to as Composition 4)

| Ex. No. | Ingredient | mg per tablet | Preparation | Remained ratio |
|---|---|---|---|---|
| 14 | PG-Powd (obtained in Ex. 3) | 10 | | |
| | Crystalline cellulose | 171 | | 87 |
| | Hydroxypropyl cellulose | 3 | tablet | (6) |
| | Carboxymethyl cellylose sodium | 10 | (wet granulation) | |
| | Talc | 4 | | |
| | Magnesium stearate | 2 | | |

(This composition is referred to as Composition 5)

| 15 | PG-Powd (obtained in Ex. 1) | 30 | | |
|---|---|---|---|---|
| | Lactose | 250 | | 87 |
| | Starch | 50 | powder | (8) |
| | D-mannitol | 100 | | |

(This composition is referred to as Composition 6)

| | | mg per capsule | | |
|---|---|---|---|---|
| 16 | PG-Powd (obtained in Ex. 1) | 30 | | |
| | Lactose | 300 | | 85 |
| | Starch | 85 | capsule | (7.5) |
| | D-mannitol | 2.5 | | |
| | Talc | 10 | | |
| | Magnesium stearate | 2.5 | | |

(This composition is referred to as Composition 7)

| 17 | Composition 1 (PG-Powd is obtained in Ex. 4) | | tablet (direct compression) | 97 (6) |
|---|---|---|---|---|
| 18 | Composition 2 (PG-Powd is obtained in Ex. 5) | | (direct compression) | 96 (5.5) |
| 19 | Composition 6 (PG-Powd is obtained in Ex. 6) | | powder | 96 (6) |
| 20 | Composition 7 (PG-Powd is obtained in Ex. 7) | | capsule | 90 (6) |
| 21 | PG-Powd (obtained in Ex. 8) | 20 | | |
| | Crystalline cellulose | 130 | | |
| | Calcium hydrogenphosphate | 87 | | |
| | Carboxymethyl cellulose sodium | 4 | tablet | 87 |
| | Light silicic anhydride | 1 | (wet granulation) | (7.5) |
| | Talc | 4 | | |
| | Magnesium stearate | 4 | | |
| 22 | Composition 3 (PG-Powd obtained in Ex. 4) | | tablet (wet granulation) | 93 (5) |

| | | mg per tablet | | |
|---|---|---|---|---|
| 23 | PG-Powd (obtained in Ex. 9) | 30 | | |
| | Crystalline cellulose | 120 | | |
| | Calcium hydrogenphosphate | 87 | tablet | 98 |
| | Carboxymethyl cellulose calcium | 4 | (direct compression) | (7) |
| | Light silicic anhydride | 1 | | |
| | Talc | 4 | | |
| | Magnesium stearate | 4 | | |

In the above table, the numbers in the parentheses in the right hand column are the remained ratios (%) of PGE in PG-Powd being solely prepared from PGE for the control of stabilization effect.

What is claimed is:

1. A stabilized prostaglandin composition comprising an active prostaglandin E group compound with an effective amount of calcium lactate and/or an effective amount of amylopectin.

2. The composition of claim 1 wherein the prostaglandin E group compound is 16(S)-methyl-20-methoxy prostaglandin $E_2$.

3. The composition of claim 1 wherein the prostaglandin E group compound is 4(R),16(R)-dimethyl prostaglandin $E_2$.

4. The composition of claim 1 wherein the prostaglandin E group compound is 4(S),16(R)-dimethyl prostaglandin $E_2$.

5. The composition of claim 1 wherein the prostaglandin E group compound is 4(R),16(S)-dimethyl prostaglandin $E_2$.

6. The composition of claim 1 wherein the prostaglandin E group compound is 4(S),16(S)-dimethyl prostaglandin $E_2$.

7. The composition of claim 1 wherein calcium lactate is 2–2000 parts by weight and/or amylopectin is 2–2000 parts by weight to one part by weight of prostaglandin E group compound.

8. A pharmaceutically acceptable preparation comprising the stabilized prostaglandin composition as claimed in claim 1 and pharmaceutically acceptable ingredients or additives for practical administration.

9. Process for the preparation of a stabilized prostaglandin composition which comprises dissolving a prostaglandin E group compound in water, organic solvent or a mixture thereof together with calcium lactate and/or amylopectin, and drying the solution to form a dry powder.

* * * * *

UNITED STATES PATENT OFFICE
CERTIFICATE OF CORRECTION

Patent No. 4,066,787　　　　　　　　　Dated January 3, 1978

Inventor(s) Kiyoshi Okazaki, et al

It is certified that error appears in the above-identified patent and that said Letters Patent are hereby corrected as shown below:

In column 5, Table 2, under "Ex. No.":  "4a" and "6a"

should read --4-- and --6--, respectively.

Signed and Sealed this

Twenty-third Day of May 1978

[SEAL]

Attest:

RUTH C. MASON　　　　　　　LUTRELLE F. PARKER
Attesting Officer　　　　Acting Commissioner of Patents and Trademarks